(12) United States Patent
Ruediger et al.

(10) Patent No.: US 7,449,476 B2
(45) Date of Patent: Nov. 11, 2008

(54) TETRAHYDROCARBOLINE ANTIVIRAL AGENTS

(75) Inventors: Edward H. Ruediger, Greenfield Park (CA); Daniel H. Deon, Brossard (CA); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 608 days.

(21) Appl. No.: 11/133,614

(22) Filed: May 20, 2005

(65) Prior Publication Data
US 2005/0267130 A1    Dec. 1, 2005

Related U.S. Application Data

(60) Provisional application No. 60/574,669, filed on May 26, 2004.

(51) Int. Cl.
C07D 471/04    (2006.01)
A61K 31/437    (2006.01)
(52) U.S. Cl. .......................................... 514/292; 546/81
(58) Field of Classification Search .................. 546/81; 514/291, 292
See application file for complete search history.

(56) References Cited

U.S. PATENT DOCUMENTS 6,469,006 B1    10/2002    Blair et al.
6,476,034 B2    11/2002    Wang et al.
6,573,262 B2    6/2003    Wallace et al.
6,632,819 B1    10/2003    Wang et al.
2005/0124623 A1    6/2005    Bender et al.

OTHER PUBLICATIONS

U.S. Appl. No. 10/762,108, filed Jan. 21, 2004, Tao Wang, et al.

*Primary Examiner*—Rita J Desai
(74) *Attorney, Agent, or Firm*—James Epperson

(57) ABSTRACT

The invention encompasses a series of tetrahydrocarboline compounds of Formula I which inhibit HIV entry by attaching to the exterior viral envelop protein gp120 and interrupting the viral entry process, possibly by interfering with the cellular receptor CD4. This action makes the compounds useful for treating HIV infection and AIDS. The invention also encompasses pharmaceutical compositions and methods for treating those infected with HIV.

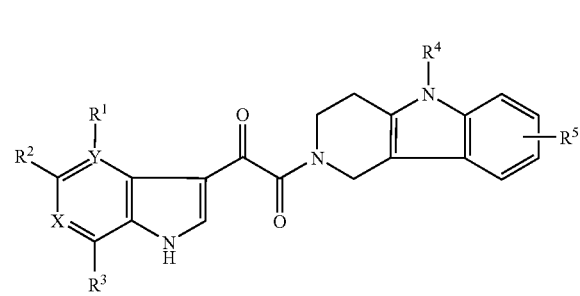

10 Claims, No Drawings

TETRAHYDROCARBOLINE ANTIVIRAL AGENTS

CROSS REFERENCE TO RELATED APPLICATIONS

This application claims the benefit of U.S. provisional application Ser. No. 60/574,669 filed May 26, 2004.

BACKGROUND OF THE INVENTION

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, 5.0 million new infections were reported, and 3.1 million people died from AIDS. Currently available drugs for the treatment of HIV include nine nucleoside reverse transcriptase (RT) inhibitors or approved single pill combinations(zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains –3TC plus AZT), Trizivir® (contains abacavir, lamivudine, and zidovudine); three non-nucleoside reverse transcriptase inhibitors: nevirapine (or Viramune®), delavirdine (or Rescriptor®) and efavirenz (or Sustiva®), and seven peptidomimetic protease inhibitors or approved formulations: saquinavir, indinavir, ritonavir, nelfinavir, amprenavir, lopinavir, and Kaletra® (lopinavir and Ritonavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections. At least 30 different classes of NNRTI have been described in the literature and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance.

The compounds of this invention inhibit HIV entry by attaching to the exterior viral envelop protein gp120 and interrupting the viral entry process, possibly by interfering with the cellular receptor CD4. Compounds in this class have been reported to have antiviral activity against a variety of laboratory and clinical strains of HIV-1 and are effective in treating HIV infection (see Hanna et al., Abstract 141 presented at the 11th Conference on Retroviruses and Opportunistic Infections, San Francisco, Calif., Feb. 8-11, 2004; Lin et al., Poster 534 presented at the 11th Conference on Retroviruses and Opportunistic Infections, San Francisco, Calif., Feb. 8-11, 2004; Hanna et al., Poster 535 presented at the 11th Conference on Retroviruses and Opportunistic Infections, San Francisco, Calif., Feb. 8-11, 2004).

N-(3-aryl-3-oxo)acetyl piperidines have been disclosed. See Blair et al., U.S. Pat. No. 6,469,006; Wang et al., U.S. Pat. No. 6,476,034; Wang et al., U.S. Pat. No. 6,632,819; Wallace et al., U.S. Pat. No. 6,573,262 (continuation-in-part application of U.S. Ser. No. 09/888,686 filed Jun. 25, 2001); Wang et al. U.S. patent application Ser. No. 10/214,982 filed Aug. 7, 2002 (continuation-in-part application of U.S. Ser. No. 10/038,306 filed Jan. 2, 2002); Wang et al. patent application WO 03/092695, published Nov. 13, 2003; Wang et al. U.S. patent application 20040063744, published Apr. 1, 2004. Nothing in these references teaches or suggests the novel compounds of this invention or their use to inhibit HIV infection.

DESCRIPTION OF THE INVENTION

The invention encompasses a series of tetrahydrocarboline compounds of Formula I including their pharmaceutically acceptable salts and solvates, their pharmaceutical compositions, and their antiviral uses.

One aspect of the invention are compounds of Formula I

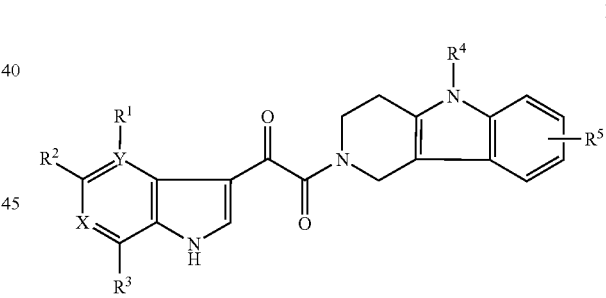

wherein:

X is CH or N;

Y is C or N;

$R^1$ is hydrogen, halo, or $C_{1-6}$alkoxy, provided that when Y is N, $R^1$ is absent;

$R^2$ is hydrogen or halo;

$R^3$ is hydrogen, halo, $C_{1-6}$alkoxy, or $CONHR^6$, or is a heteroaryl moiety selected from the group consisting of pyrrolyl, imidazolyl, triazolyl, pyridinyl, pyrimidinyl, pyrazinyl, and tetrazolyl, and where the heteroaryl moiety is substituted with 0-2 $C_{1-6}$alkyl groups;

$R^4$ is hydrogen, $C_{1-6}$alkyl, or phenyl;

$R^5$ is hydrogen, halo, trifluoromethyl, trifluoromethoxy, $C_{1-6}$alkyl, or $C_{1-6}$alkoxy; and $R^6$ is hydrogen or $C_{1-6}$alkyl;

or a pharmaceutically acceptable salt or solvate thereof.

Another aspect of the invention are compounds where X is N.

Another aspect of the invention are compounds of Formula I where X is N and Y is C.

Another aspect of the invention are compounds of Formula I where $R^1$ is methoxy.

Another aspect of the invention are compounds of Formula I where $R^2$ is hydrogen, fluorine, or chlorine.

Another aspect of the invention are compounds of Formula I where wherein $R^3$ is methoxy or triazolyl where the triazolyl moiety is substituted with 0-1 $C_{1-6}$alkyl.

Another aspect of the invention are compounds of Formula I where $R^4$ is phenyl.

Another aspect of the invention are compounds of Formula I where $R^5$ is fluoro or trifluoromethyl.

Some compounds of the invention are 2,3,4,5-tetrahydro-2-[2-(1H-indol-3-yl)-1,2-dioxoethyl]-1H-pyrido[4,3-b]indole;

2,3,4,5-tetrahydro-2-[2-[4-methoxy-7-(5-methyl-1H-1,2,4-triazol-1-yl)-1H-pyrrolo[2,3-c]pyridin-3-yl]-1,2-dioxoethyl]-5-phenyl-1H-pyrido[4,3-b]indole;

2-[2-(4,7-dimethoxy-1H-pyrrolo[2,3-c]pyridin-3-yl)-1,2-dioxoethyl]-2,3,4,5-tetrahydro-5-phenyl-1H-pyrido[4,3-b]indole;

2-[2-(4,7-dimethoxy-1H-pyrrolo[2,3-c]pyridin-3-yl)-1,2-dioxoethyl]-2,3,4,5-tetrahydro-1H-pyrido[4,3-b]indole;

2-[2-(4,7-dimethoxy-1H-pyrrolo[2,3-c]pyridin-3-yl)-1,2-dioxoethyl]-8-fluoro-2,3,4,5-tetrahydro-1H-pyrido[4,3-b]indole;

2-[2-(4,7-dimethoxy-1H-pyrrolo[2,3-c]pyridin-3-yl)-1,2-dioxoethyl]-8-fluoro-2,3,4,5-tetrahydro-5-methyl-1H-pyrido[4,3-b]indole;

2-[2-(4,7-dimethoxy-1H-pyrrolo[2,3-c]pyridin-3-yl)-1,2-dioxoethyl]-2,3,4,5-tetrahydro-8-(trifluoromethyl)-1H-pyrido[4,3-b]indole;

2,3,4,5-tetrahydro-2-[2-[4-methoxy-7-(3-methyl-1H-1,2,4-triazol-1-yl)-1H-pyrrolo[2,3-c]pyridin-3-yl]-1,2-dioxoethyl]-5-phenyl-1H-pyrido[4,3-b]indole;

8-fluoro-2,3,4,5-tetrahydro-2-[2-[4-methoxy-7-(3-methyl-1H-1,2,4-triazol-1-yl)-1H-pyrrolo[2,3-c]pyridin-3-yl]-1,2-dioxoethyl]-5-phenyl-1H-pyrido[4,3-b]indole; and 8-fluoro-2,3,4,5-tetrahydro-2-[2-[4-methoxy-7-(1H-1,2,3-triazol-1-yl)-1H-pyrrolo[2,3-c]pyridin-3-yl]-1,2-dioxoethyl]-5-phenyl-1H-pyrido[4,3-b]indole.

"Alkyl," "alkoxy" and related terms with an alkyl moiety include straight and branched configurations. "Aryl" includes carbocyclic and heterocyclic aromatic ring systems.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, lysine, arginine, N-methylglucamine, and zinc.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

Synthetic Methods

The compounds of this invention can be made according to the schemes provided and other reactions known in the art. Schemes 1-3 illustrate procedures for making and modifying some tetrahydrocarbolines. Other tetrahydrocarboline syntheses are known in the art. Scheme 4 illustrates a procedure for attaching a tetrahydrocarboline to a substituted acetic acid.

Scheme 1.

Scheme 2.

Scheme 3.

Method A (R = Me):
NaH, THF; MeI

Method B (R = Ph):
PhI, CuI, K₃PO₄
(MeHNCH₂)₂, PhMe

-continued

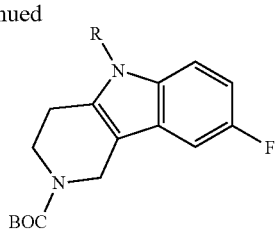

Scheme 4.

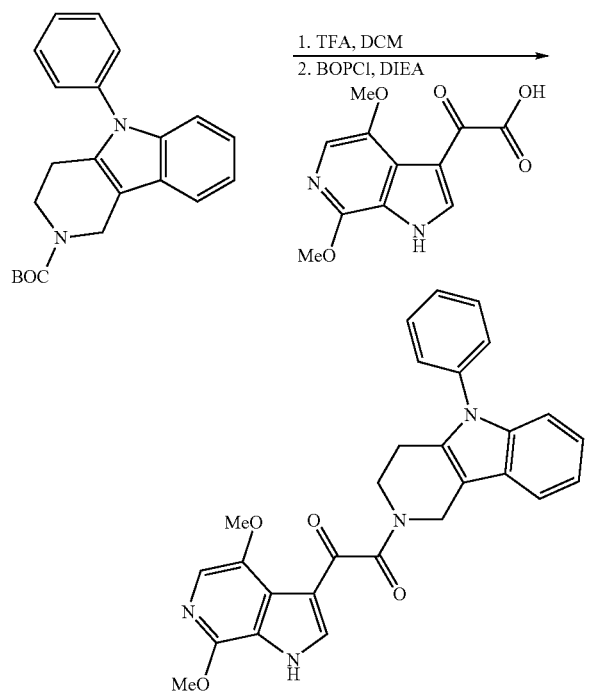

4-Azaindole and 4,6-diazaindole intermediates can be made according to methods described in U.S. Pat. Nos. 6,476, 034; 6,632,819; U.S. patent application Ser. No. 10/621,139, filed Jul. 16, 2003; U.S. patent application Ser. No. 10/214, 982, filed Aug. 7, 2002; U.S. patent application Ser. No. 10/630,278, filed Jul. 30, 2003; and U.S. patent application Ser. No. 60/525,624, filed Nov. 26, 2003.

Cyanomethyl analogs of intermediates 4, 6, and 7 can be made by removing the protecting group and treating the resulting amine with chloroacetonitrile and triethylamine. The cyanomethyl intermediates can be coupled with a variety of indole-3-carboxylic methyl esters to generate additional compounds of Formula I.

Biological Methods

Cells: (virus production) human embryonic kidney cell line, 293, was propagated in Dulbecco's Modified Eagle Medium (Invitrogen, Carlsbad, Calif.) containing 10% fetal Bovine serum (FBS, Sigma, St. Louis, Mo.); (virus infection) human epithelial cell line, HeLa, expressing the HIV-1 receptor CD4 was propagated in Dulbecco's Modified Eagle Medium (Invitrogen, Carlsbad, Calif.) containing 10% fetal Bovine serum (FBS, Sigma, St. Louis, Mo.) and supplemented with 0.2 mg/mL Geneticin (Invitrogen, Carlsbad, Calif.).

Virus: single-round infectious reporter virus was produced by co-transfecting human embryonic kidney 293 cells with an HIV-1 envelope DNA expression vector and a proviral cDNA containing an envelope deletion mutation and the luciferase reporter gene inserted in place of HIV-1 nef sequences. Transfections were performed using lipofectAMINE PLUS reagent as described by the manufacturer (Invitrogen, Carlsbad, Calif.).

Experiment: HeLa CD4 cells were plated in 96 well plates at a cell density of 1×104 cells per well in 100 μl Dulbecco's Modified Eagle Medium containing 10% fetal Bovine serum and incubated overnight. Compound was added in a 2 μl dimethylsulfoxide solution, so that the final assay concentration would be ≦10 μM. Single-round infectious reporter virus (100 μL) in Dulbecco's Modified Eagle Medium was then added to the plated cells and compound at an approximate multiplicity of infection (MOI) of 0.01, resulting in a final volume of 200 μl per well. Virally-infected cells were incubated at 37 degrees Celsius, in a CO2 incubator, and harvested 72 h after infection. Viral infection was monitored by measuring luciferase expression from viral DNA in the infected cells using a luciferase reporter gene assay kit, as described by the manufacturer (Roche Molecular Biochemicals, Indianapolis, Ind.). Infected cell supernatants were removed and 50 μl of lysis buffer was added per well. After 15 minutes, 50 μl of freshly-reconstituted luciferase assay reagent was added per well. Luciferase activity was then quantified by measuring luminescence using a Wallac microbeta luminescence reader.

The percent inhibition for each compound was calculated by quantifying the level of luciferase expression in cells infected in the presence of each compound as a percentage of that observed for cells infected in the absence of compound and subtracting such a determined value from 100. The effective concentration for fifty percent inhibition ($EC_{50}$) was calculated with Microsoft Excel Xlfit curve fitting software. For each compound, curves were generated from percent inhibition calculated at 10 different concentrations by using a four paramenter logistic model (model 205). The $EC_{50}$ data for the compounds is shown in Table 1. Table 1.

TABLE 1

| Example | $EC_{50}$ |
| --- | --- |
| 1 | A |
| 2 | C |
| 3 | C |
| 4 | A |
| 5 | B |
| 6 | A |
| 7 | A |
| 8 | A |
| 9 | A |

$EC_{50}$ < 1 μM = A; 1-5 μM = B; >5 μM = C; >0.5 μM = D.

Pharmaceutical Composition and Methods of Use

The compounds of this invention inhibit HIV entry by attaching to the exterior viral envelop protein gp120 and interrupting viral entry, possibly by interfering with recognition of the cellular receptor CD4. Compounds in this class have been reported to have antiviral activity against a variety of laboratory and clinical strains of HIV-1 and are effective in treating HIV infection (see Hanna et al., Abstract 141 presented at the 11th Conference on Retroviruses and Opportunistic Infections, San Francisco, Calif., Feb. 8-11, 2004; Lin et al., Poster 534 presented at the 11th Conference on Retroviruses and Opportunistic Infections, San Francisco, Calif., Feb. 8-11, 2004; Hanna et al., Poster 535 presented at the 11th Conference on Retroviruses and Opportunistic Infections, San Francisco, Calif., Feb. 8-11, 2004).

Accordingly, another aspect of the invention is a method for treating HIV infection in a human patient comprising administering a therapeutically effective amount of a compound of Formula I, or a pharmaceutically acceptable salt or solvate thereof, with a pharmaceutically acceptable carrier.

Another aspect of the invention is a method for treating HIV infection in a human patient comprising administering a therapeutically effective amount of a compound of Formula I, or a pharmaceutically acceptable salt or solvate thereof, with a therapeutically effective amount of at least one other agent used for treatment of AIDS or HIV infection. Some suitable agents are nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a composition for treating HIV infection in a human patient comprising administering a therapeutically effective amount of a compound of Formula I, or a pharmaceutically acceptable salt or solvate thereof, with a pharmaceutically acceptable carrier.

"Combination," "coadministration," "concurrent," and similar terms referring to the administration of compounds of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen" "HIV infection," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, Compound 1 will generally be given in a daily dose of 1-100 mg/kg body weight daily in conjunction with other agents. The other agents generally will be given in the amounts used therapeutically. The specific dosing regime, however, will be determined by a physician using sound medical judgement.

Table 2 lists some agents useful in treating AIDS and HIV infection which are suitable for this invention.

TABLE 2

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |

TABLE 2-continued

| DRUG NAME | MANUFACTURER | INDICATION |
|---|---|---|
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptaseinhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine | Boeheringer | HIV infection, AIDS, |

TABLE 2-continued

| DRUG NAME | MANUFACTURER | INDICATION |
|---|---|---|
| (RT inhibitor) | Ingleheim | ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMVinfections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |

IMMUNOMODULATORS

| DRUG NAME | MANUFACTURER | INDICATION |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle | Rorer | Seropositive HIV |

TABLE 2-continued

| DRUG NAME | MANUFACTURER | INDICATION |
|---|---|---|
| Immunostimulant | | |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma AIDS, in combination w/AZT |
| Granulocyte Colony Stimulating Factor | Amgen | |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

LC/MS Method (compound identification). Column: Primesphere C-18 HC 4.6×33 mm column; Standard LC Run Conditions (used unless otherwise noted): Gradient: 100% Solvent A/0% Solvent B to 0% Solvent A/100% Solvent B; Solvent A=10% MeCN-90% $H_2O$ (5 mM NH4OAc), Solvent B=90% MeCN-10% H2O (5 mM NH4OAc); Gradient time: 2 minutes; Stop time: 3 min; Flow rate: 4 mL/min; Detector Wavelength: 220 nm.

Preparative HPLC Method (i.e., compound purification). Column: YMC Pack C-18 20×100 mm column; Standard LC Run Conditions (used unless otherwise noted): Gradient: 90% Solvent A/10% Solvent B to 0% Solvent A/100% Solvent B; Solvent A=10% MeCN-90% H2O (5 mM NH4OAc), Solvent B=90% MeCN-10% H2O (5 mM NH4OAc); Gradient time: 7 min; Stop time: 10 min; Flow rate: 20 mL/min; Detector Wavelength: 220 nm. Alternate solvent system: Solvent A=10% MeCN-90% H2O-0.1% TFA; Solvent B=90% MeCN-10% H2O-0.1% TFA.

Compounds purified by preparative HPLC were diluted in MeOH or DMF (2 mL) and purified using the following methods on a Shimadzu LC-10A automated preparative HPLC system or on a Shimadzu LC-8A automated preparative HPLC system with detector (SPD-10AV UV-VIS) wavelength and solvent systems (A and B) the same as above.

Intermediate 1

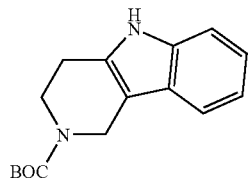

Preparation of 1,3,4,5-Tetrahydropyrido[4,3-b]indole-2-carboxylic acid tert-butyl ester. General Method: A mixture of 2-iodoaniline (0.315 g, 1.44 mmol), 4-oxo-1-piperidinecarboxylic acid tert-butyl ester (0.860 g, 4.31 mmol), 1,4-diazabicyclo[2.2.2]octane (Dabco™) (0.483 mL, 4.31 mmol) and palladium acetate (0.016 g, 0.072 mmol) in dry DMF (7 mL) was degassed via vacuum/argon purging, and then it was heated to 110° C. for 3.5 h. The reaction mixture was subsequently cooled to room temperature and partitioned between ethyl acetate and water. The organic layer was separated, dried ($MgSO_4$), filtered and evaporated to dryness. The residue was chromatographed ($SiO_2$/hexanes:ethyl acetate, 1:1) to give the title compound (0.068 g, 17%) as an off-white solid. $^1$H NMR (400 MHz, $CDCl_3$) δ 7.88 (s, 1H), 7.45 (d, J=7.6 Hz, 1H), 7.31 (d, J=7.6 Hz, 1H), 7.12 (m, 2H), 4.64 (s, 2H), 3.82 (s, 2H), 2.82 (s, 2H), 1.50 (s, 9H); LCMS: m/e 273 $(M+H)^+$.

Intermediate 2

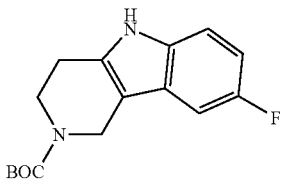

Preparation of 8-Fluoro-1,3,4,5-tetrahydropyrido[4,3-b]indole-2-carboxylic acid tert-butyl ester. Prepared according to the general method to give the title compound (87% yield) as a clear oil. $^1$H NMR (400 MHz, CDCl$_3$) δ 7.90 (s, 1H), 7.20 (dd, J=8.8, 4.3 Hz, 1H), 7.08 (d, J=8.1 Hz, 1H), 6.87 (m, 1H), 4.58 (s, 2H), 3.81 (s, 2H), 2.81 (s, 2H), 1.50 (s, 9H); LCMS: m/e 291 (M+H)$^+$.

Intermediate 3

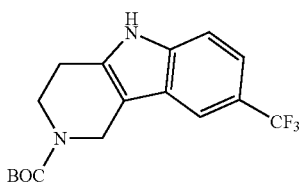

Preparation of 8-Trifluoromethyl-1,3,4,5-tetrahydropyrido[4,3-b]indole-2-carboxylic acid tert-butyl ester. Prepared according to the general method to give the title compound (17% yield) as a white solid. $^1$H NMR (400 MHz, CDCl$_3$) δ 8.62 (m, 1H), 7.70 (m, 1H), 7.36 (s, 2H), 4.66 (s, 2H), 3.83 (m, 2H), 2.83 (t, J=5.8 Hz, 2H), 1.52 (s, 9H); LCMS: m/e 341 (M+H)$^+$.

Intermediate 4

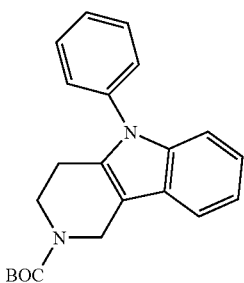

Preparation of 5-Phenyl-1,3,4,5-tetrahydro-pyrido[4,3-b]indole-2-carboxylic acid tert-butyl ester. A mixture of 1,1-diphenylhydrazine hydrochloride (0.365 g, 1.65 mmol) and 4-oxo-1-piperidinecarboxylic acid tert-butyl ester (0.329 g, 1.65 mmol) in pyridine (3 mL) was heated in a sealed tube at 120° C. with stirring for 3 h. The reaction mixture was subsequently cooled to room temperature and partitioned between ethyl acetate and water. The organic layer was separated, dried (MgSO$_4$), filtered and evaporated to dryness. The residue was chromatographed (SiO$_2$/hexanes:ethyl acetate, 3:2) to give the title compound (0.214 g, 37%) as a brown oil.

$^1$H NMR (400 MHz, CDCl$_3$) δ 7.51 (m, 2H), 7.40 (m, 1H), 7.35 (m, 2H), 7.26 (m, 2H), 7.14 (m, 2H), 4.72 (s, 2H), 3.78 (s, 2H), 2.71 (s, 2H), 1.51 (s, 9H); LCMS: m/e 349 (M+H)$^+$.

Intermediate 6

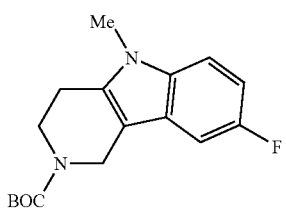

Preparation of 8-Fluoro-5-methyl-1,3,4,5-tetrahydro-pyrido[4,3-b]indole-2-carboxylic acid tert-butyl ester. To a suspension of NaH (80% in oil, 0.0190 g, 0.633 mmol) in dry THF (1 mL), was added a solution of 8-fluoro-1,3,4,5-tetrahydropyrido[4,3-b]indole-2-carboxylic acid tert-butyl ester (0.114 g, 0.393 mmol) in THF (4 mL) via cannula. The reaction mixture was allowed to stir at room temperature for 5 min and then iodomethane (0.098 mL, 1.57 mmol) was added. The resulting mixture was stirred for 2 h and then it was quenched with saturated aqueous ammonium chloride and extracted with ethyl acetate. The organic phase was separated, dried (MgSO$_4$), filtered and concentrated to dryness to give the title compound (0.109 g, 91%) as a yellow oil which was used without further purification. LCMS: m/e 305 (M+H)$^+$.

Intermediate 7

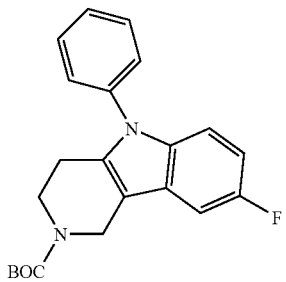

Preparation of 8-Fluoro-5-phenyl-1,3,4,5-tetrahydro-pyrido[4,3-b]indole-2-carboxylic acid tert-butyl ester. A mixture of 8-fluoro-1,3,4,5-tetrahydropyrido[4,3-b]indole-2-carboxylic acid tert-butyl ester (0.455 g, 1.57 mmol), CuI (0.012 g, 0.065 mmol) and K$_3$PO$_4$ (0.579 g, 2.73 mmol) was suspended in toluene (5 mL) under Ar. To this mixture was added iodobenzene (0.145 mL, 1.30 mmol) and N,N'-dimethylethylenediamine (0.028 mL, 0.26 mmol) and then the reaction vessel was quickly sealed and the mixture was heated with stirring at 150° C. (oil bath temperature) for 16 h. The cooled reaction mixture was subsequently filtered (Celite) and the filtrate was concentrated to dryness. The residue was purified by flash chromatography (SiO$_2$/hexanes-ethyl acetate, 80:20 to 20:80) to give the title compound (0.267 g, 46%) as a white foam. $^1$H NMR (400 MHz, CDCl$_3$) δ 7.51 (m, 2H), 7.41 (m, 1H), 7.33 (m, 2H), 7.15 (m, 2H), 6.87 (m, 1H), 4.66 (s, 2H), 3.77 (m, 2H), 2.70 (m, 2H), 1.51 (s, 9H); LCMS: m/e 367 (M+H)$^+$.

EXAMPLE 1

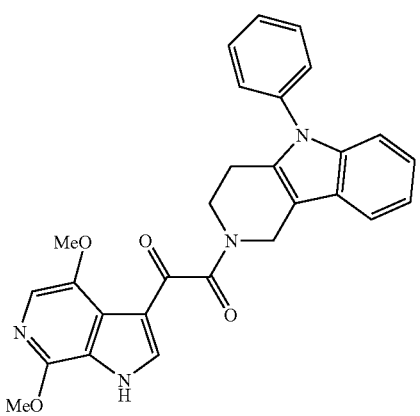

1-(5-Phenyl-1,3,4,5-tetrahydro-pyrido[4,3-b]indol-2-yl)-2-(4,7-dimethoxy-6-azaindol-3-yl)-ethane-1,2-dione. General Method: A solution of 5-phenyl-1,3,4,5-tetrahydro-pyrido[4,3-b]indole-2-carboxylic acid tert-butyl ester (0.054 g, 0.155 mmol) in dry $CH_2Cl_2$ (2 mL) was treated with TFA (0.20 mL). After stirring the mixture for 1 h, the solvent was evaporated in vacuo and the residue was dissolved in $CHCl_3$ (5 mL). To this mixture was added 4,7-dimethoxy-6-azaindol-3-yl-oxoacetic acid (0.042 g, 0.155 mmol), i-Pr2NEt (0.27 mL, 1.55 mmol) and then BOP-Cl (0.039 g, 0.153 mmol). The mixture was allowed to stir at room temperature for 2 h and then the solvent was removed in vacuo. The residue was partitioned with EtOAc-H2O, the organic phase was separated and the aqueous phase was re-extracted with EtOAc (2×). The combined organic layers were washed (H2O, brine), dried (Na2SO4) and evaporated. The residue was purified by preparative HPLC to give the title compound (0.025 g, 33%) as a white solid. $^1$H NMR (400 MHz, $CDCl_3$) δ 9.27 (s, 0.67H), 9.22 (s, 0.33H), 8.06 (d, J=3.0 Hz, 0.67H), 8.00 (d, J=3.0 Hz, 0.33H), 7.59-7.07 (m, 10H), 4.11 (m, 1H), 4.05 (s, 3H), 3.88 (s, 1H), 3.85 (m, 2H), 3.72 (s, 2H), 2.88 (m, 1H), 2.78 (m, 2H); LCMS: m/e 481 (M+H)+.

EXAMPLE 2

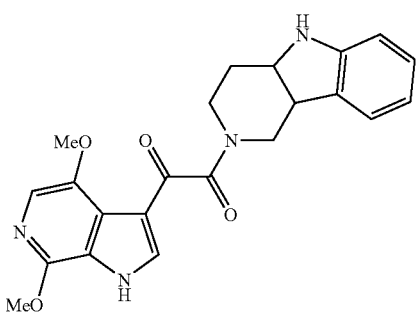

1-(1,3,4,5-Tetrahydro-pyrido[4,3-b]indol-2-yl)-2-(4,7-dimethoxy-6-azaindol-3-yl)-ethane-1,2-dione. Prepared according to the general method to give the title compound (53% yield) as a white solid. $^1$H NMR (400 MHz, $CDCl_3$) δ 9.23 (s, 0.67H), 9.14 (s, 0.33H), 8.06 (d, J=3.0 Hz, 0.70H), 7.96 (d, J=3.0 Hz, 0.30H), 7.92 (s, 0.40H), 7.89 (s, 0.60H), 7.52-6.99 (m, 5H), 4.15 (m, 1H), 4.05 (s, 2H), 4.04 (s, 1H), 3.89 (m, 2H), 3.83 (s, 1H), 3.67 (s, 2H), 3.00 (m, 1H), 2.89 (m, 2H); LCMS: m/e 405 (M+H)+.

EXAMPLE 3

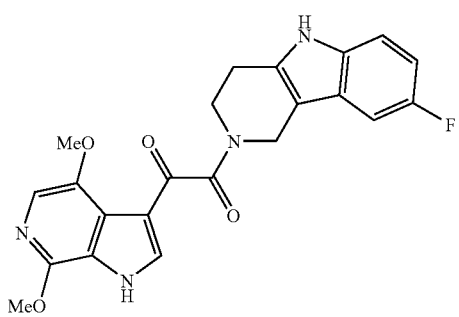

1-(8-Fluoro-1,3,4,5-tetrahydro-pyrido[4,3-b]indol-2-yl)-2-(4,7-dimethoxy-6-azaindol-3-yl)-ethane-1,2-dione. Prepared according to the general method to give the title compound (15% yield) as a white solid. $^1$H NMR (400 MHz, DMSO-d6) δ 11.12 (s, 0.33H), 11.06 (s, 0.67H), 8.17 (s, 0.56H), 8.09 (s, 0.44H), 7.42 (s, 0.38H), 7.39 (s, 0.62H), 7.32-7.24 (m, 1H), 6.91-6.83 (m, 1H), 3.99 (m, 1H), 3.97 (s, 2H), 3.96 (s, 1H), 3.74 (s, 1H), 3.70 (m, 2H), 3.59 (s, 2H), 2.93 (m, 1H), 2.76 (m, 2H); LCMS: m/e 423 (M+H)+.

EXAMPLE 4

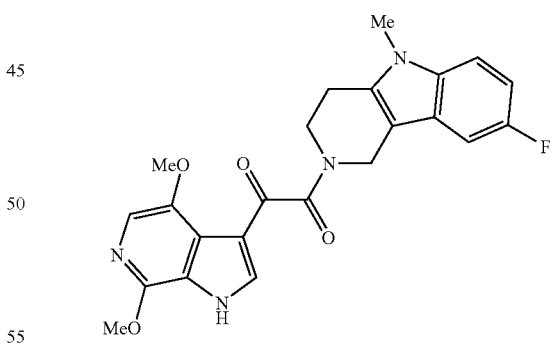

1-(8-Fluoro-5-methyl-1,3,4,5-tetrahydro-pyrido[4,3-b]indol-2-yl)-2-(4,7-dimethoxy-6-azaindol-3-yl)-ethane-1,2-dione. Prepared according to the general method to give the title compound (36% yield) as a white solid. $^1$H NMR (400 MHz, $CDCl_3$) δ 9.27 (s, 0.67H), 9.17 (s, 0.33H), 8.04 (d, J=3.5 Hz, 0.69H), 7.96 (d, J=3.5 Hz, 0.31H), 7.42 (s, 0.25H), 7.39 (s, 0.75H), 4.16 (m, 1H), 4.03 (s, 2H), 4.02 (s, 1H), 3.90 (m, 2H), 3.84 (s, 1H), 3.69 (s, 2H), 3.65 (s, 1H), 3.62 (s, 2H), 2.97 (m, 1H), 2.88 (m, 2H); LCMS: m/e 437 (M+H)+.

EXAMPLE 5

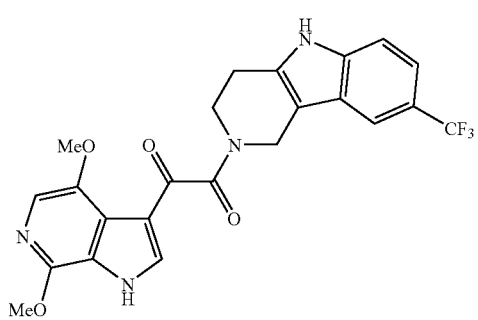

1-(8-Trifluoromethyl-1,3,4,5-tetrahydro-pyrido[4,3-b]indol-2-yl)-2-(4,7-dimethoxy-6-azaindol-3-yl)-ethane-1,2-dione. Prepared according to the general method to give the title compound (60% yield) as a white solid. $^1$H NMR (400 MHz, CDCl$_3$) δ 13.04 (m, 0.67H), 12.96 (m, 0.33H), 11.50 (s, 0.33H), 11.46 (s, 0.67H), 8.18 (d, J=3.5 Hz, 0.63H), 8.10 (d, J=3.5 Hz, 0.37H), 7.95 (s, 0.67H), 7.80 (s, 0.33H), 7.51-7.31 (m, 3H), 4.01 (m, 1H), 3.98 (s, 2H), 3.97 (s, 1H), 3.74 (s, 1H), 3.72 (m, 2H), 3.59 (s, 2H), 2.97 (m, 1H), 2.80 (m, 2H); LCMS: m/e 473 (M+H)+.

EXAMPLE 6

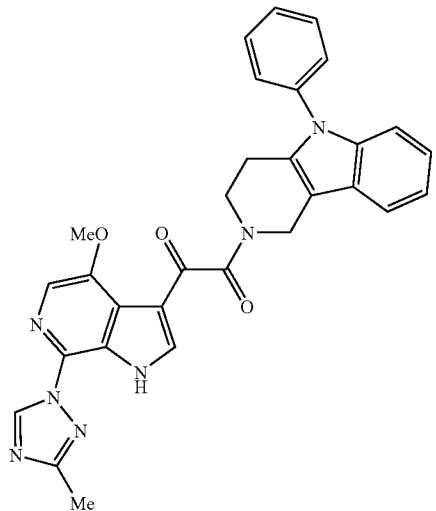

1-(5-Phenyl-1,3,4,5-tetrahydro-pyrido[4,3-b]indol-2-yl)-2-[4-methoxy-7-(3-methyl-1,2,4-triazol-1-yl)-6-azaindol-3-yl]-ethane-1,2-dione. Prepared according to the general method to give the title compound (56% yield) as a white solid. $^1$H NMR (400 MHz, CDCl$_3$) δ 11.01 (s, 0.7H), 10.96 (s, 0.3H), 9.13 (s, 1H), 8.28 (d, J=3.0 Hz, 0.7H), 8.21 (d, J=3.5 Hz, 0.3H), 7.73 (s, 0.3H), 7.70 (s, 0.7H), 7.59-7.04 (m, 9H), 4.13 (t, J=5.8 Hz, 1H), 3.98 (s, 1H), 3.89 (t, J=5.6 Hz, 2H), 3.84 (s, 2H), 2.90 (m, 1H), 2.81 (m, 2H), 2.57 (s, 2H), 2.56 (s, 1H); LCMS: m/e 532 (M+H)+.

EXAMPLE 7

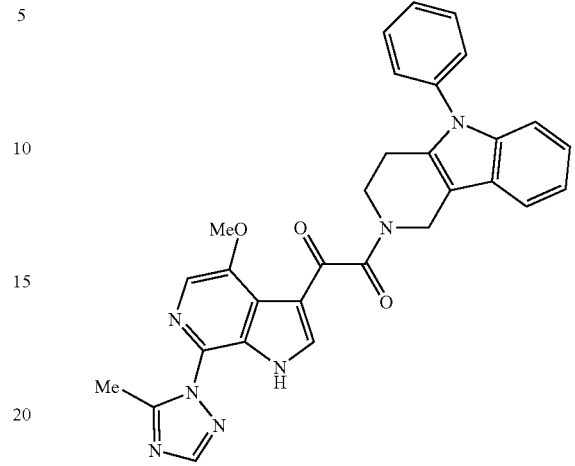

1-(5-Phenyl-1,3,4,5-tetrahydro-pyrido[4,3-b]indol-2-yl)-2-[4-methoxy-7-(5-methyl-1,2,4-triazol-1-yl)-6-azaindol-3-yl]-ethane-1,2-dione. Prepared according to the general method to give the title compound (41% yield) as a light yellow solid. $^1$H NMR (400 MHz, CDCl$_3$) δ 10.92 (s, 0.67H), 10.87 (s, 0.33H), 8.27 (d, J=3.0 Hz, 1H), 8.17 (d, J=3.0 Hz, 1H), 7.81 (s, 0.33H), 7.79 (s, 0.67H), 7.59-7.08 (m, 9H), 4.14 (m, 1H), 3.90 (m, 2H), 3.87 (s, 3H), 3.08 (s, 3H), 2.90 (m, 1H), 2.82 (m, 2H); LCMS: m/e 532 (M+H)+.

EXAMPLE 8

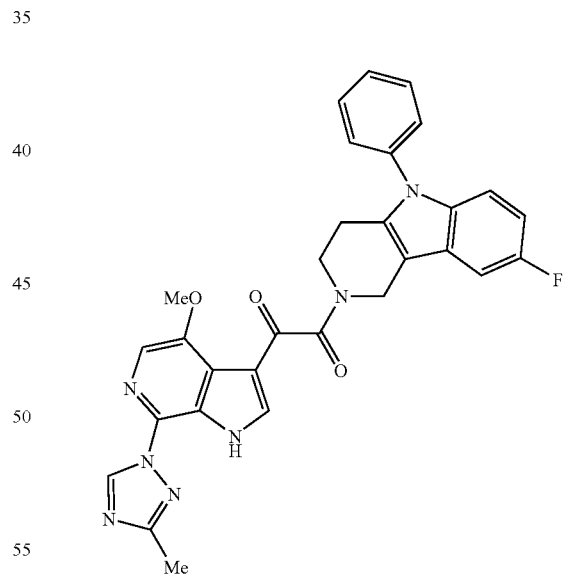

1-(8-Fluoro-5-phenyl-1,3,4,5-tetrahydro-pyrido[4,3-b]indol-2-yl)-2-[4-methoxy-7-(3-methyl-1,2,4-triazol-1-yl)-6-azaindol-3-yl]-ethane-1,2-dione. Prepared according to the general method to give the title compound (37% yield) as a white solid. $^1$H NMR (400 MHz, CDCl$_3$) 11.03 (s, 0.64H), 11.00 (s, 0.36H), 9.10 (s, 1H), 8.23 (d, J=3.5 Hz, 0.67H), 8.22 (d, J=3.0 Hz, 0.33H), 7.74 (s, 0.29H), 7.71 (s, 0.71H), 7.57-6.84 (m, 9H), 4.13 (m, 1H), 3.99 (s, 1H), 3.88 (m, 2H), 3.86 (s, 2H), 2.88 (m, 1H), 2.80 (m, 2H), 2.56 (s, 2H), 2.55 (s, 1H); LCMS: m/e 550 (M+H)+.

EXAMPLE 9

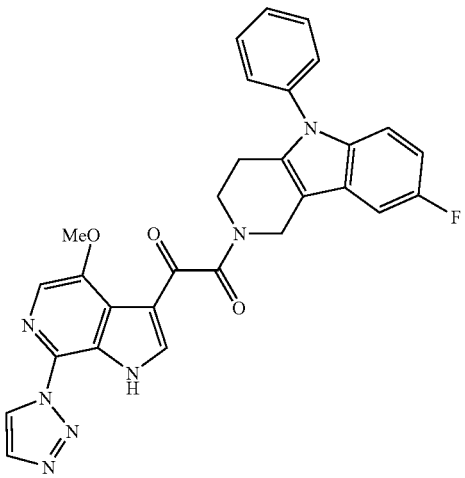

1-(8-Fluoro-5-phenyl-1,3,4,5-tetrahydro-pyrido[4,3-b]indol-2-yl)-2-[4-methoxy-7-(1,2,3-triazol-1-yl)-6-azaindol-3-yl]-ethane-1,2-dione. Prepared according to the general method to give the title compound (9% yield) as a white solid. $^1$H NMR (400 MHz, CDCl3) 11.05 (s, 0.67H), 11.01 (s, 0.33H), 8.76 (s, 1H), 8.35 (m, 0.72H), 8.29 (m, 0.28H), 7.94 (s, 1H), 7.86 (s, 0.25H), 7.83 (s, 0.75H), 7.61-6.88 (m, 8H), 4.17 (s, 1H), 4.07 (s, 1H), 3.94 (s, 2H), 3.92 (m, 2H), 2.92 (m, 1H), 2.85 (m, 2H); LCMS: m/e 536 (M+H)+.

We claim:

1. A compound of Formula I

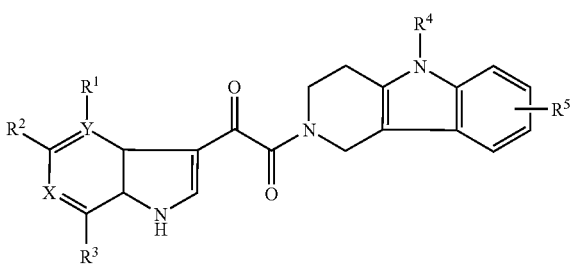

wherein:

X is CH or N;
Y is C or N;
$R^1$ is hydrogen, halo, or $C_{1-6}$alkoxy, provided that when Y is N, $R^1$ is absent;
$R^2$ is hydrogen or halo;
$R^3$ is hydrogen, halo, $C_{1-6}$alkoxy, or CONHR$^6$, or is a heteroaryl moiety selected from the group consisting of pyrrolyl, imidazolyl, triazolyl, pyridinyl, pyrimidinyl, pyrazinyl, and tetrazolyl, and where the heteroaryl moiety is substituted with 0-2 $C_{1-6}$alkyl groups;
$R^4$ is hydrogen, $C_{1-6}$alkyl, or phenyl;
$R^5$ is hydrogen, halo, trifluoromethyl, trifluoromethoxy, $C_{1-6}$alkyl, or $C_{1-6}$alkoxy; and
$R^6$ is hydrogen or $C_{1-6}$alkyl;
or a pharmaceutically acceptable salt thereof.

2. A compound of claim 1 where X is N.

3. A compound of claim 1 where X is N and Y is C.

4. A compound of claim 1 where $R^1$ is methoxy.

5. A compound of claim 1 where $R^2$ is hydrogen, fluorine, or chlorine.

6. A compound of claim 1 where $R^3$ is methoxy or triazolyl where the triazolyl moiety is substituted with 0-1 $C_{1-6}$alkyl.

7. A compound of claim 1 where $R^4$ is phenyl.

8. A compound of claim 1 where $R^5$ is fluoro or trifluoromethyl.

9. A compound of claim 1 selected from the group consisting of 2,3,4,5-tetrahydro-2-[2-(1H-indol-3-yl)-1,2-dioxoethyl]-1H-pyrido[4,3-b]indole;

2,3,4,5-tetrahydro-2-[2-[4-methoxy-7-(5-methyl-1H-1,2,4-triazol-1-yl)-1H-pyrrolo[2,3-c]pyridin-3-yl]-1,2-dioxoethyl]-5-phenyl-1H-pyrido[4,3-b]indole;

2-[2-(4,7-dimethoxy-1H-pyrrolo[2,3-c]pyridin-3-yl)-1,2-dioxoethyl]-2,3,4,5-tetrahydro-5-phenyl-1H-pyrido[4,3-b]indole;

2-[2-(4,7-dimethoxy-1H-pyrrolo[2,3-c]pyridin-3-yl)-1,2-dioxoethyl]-2,3,4,5-tetrahydro-1H-pyrido[4,3-b]indole;

2-[2-(4,7-dimethoxy-1H-pyrrolo[2,3-c]pyridin-3-yl)-1,2-dioxoethyl]-8-fluoro-2,3,4,5-tetrahydro-1H-pyrido[4,3-b]indole;

2-[2-(4,7-dimethoxy-1H-pyrrolo[2,3-c]pyridin-3-yl)-1,2-dioxoethyl]-8-fluoro-2,3,4,5-tetrahydro-5-methyl-1H-pyrido[4,3-b]indole;

2-[2-(4,7-dimethoxy-1H-pyrrolo[2,3-c]pyridin-3-yl)-1,2-dioxoethyl]-2,3,4,5-tetrahydro-8-(trifluoromethyl)-1H-pyrido[4,3-b]indole;

2,3,4,5-tetrahydro-2-[2-[4-methoxy-7-(3-methyl-1H-1,2,4-triazol-1-yl)-1H-pyrrolo[2,3-c]pyridin-3-yl]-1,2-dioxoethyl]-5-phenyl-1H-pyrido[4,3-b]indole;

8-fluoro-2,3,4,5-tetrahydro-2-[2-[4-methoxy-7-(3-methyl-1H-1,2,4-triazol-1-yl)-1H-pyrrolo[2,3-c]pyridin-3-yl]-1,2-dioxoethyl]-5-phenyl-1H-pyrido[4,3-b]indole; and 8-fluoro-2,3,4,5-tetrahydro-2-[2-[4-methoxy-7-(1H-1,2,3-triazol-1-yl)-1H-pyrrolo[2,3-c]pyridin-3-yl]-1,2-dioxoethyl]-5-phenyl-1H-pyrido[4,3-b]indole;

or a pharmaceutically acceptable salt thereof.

10. A pharmaceutical composition comprising a compound of claim 1 and a pharmaceutically acceptable carrier.

* * * * *